United States Patent [19]

Sanderson et al.

[11] Patent Number: 5,180,864

[45] Date of Patent: * Jan. 19, 1993

[54] PROCESS FOR OLIGOMERIZING OLEFINS USING AN ALUMINUM NITRATE-TREATED ACIDIC CLAY

[75] Inventors: John R. Sanderson, Leander; John F. Knifton, Austin, both of Tex.

[73] Assignee: Texaco Chemical Company, White Plains, N.Y.

[*] Notice: The portion of the term of this patent subsequent to Oct. 1, 2008 has been disclaimed.

[21] Appl. No.: 516,870

[22] Filed: Apr. 30, 1990

[51] Int. Cl.$^5$ .......................... C10L 1/16; C07C 2/02
[52] U.S. Cl. .................................... 585/10; 585/255; 585/522; 585/523; 585/533; 585/18
[58] Field of Search ................... 585/18, 10, 255, 522, 585/523, 533

[56] References Cited

U.S. PATENT DOCUMENTS

| | | | |
|---|---|---|---|
| 1,919,722 | 7/1988 | Hyman | 585/533 |
| 2,543,016 | 2/1951 | Grosse | 585/255 |
| 2,574,895 | 1/1951 | Stecker | 585/533 |
| 2,951,087 | 8/1960 | Hauser et al. | 502/62 |
| 3,412,039 | 11/1968 | Miller | 252/428 |
| 3,432,571 | 3/1969 | Noddings et al. | 260/641 |
| 3,459,815 | 8/1969 | Noddings et al. | 260/641 |
| 3,845,150 | 10/1974 | Yan et al. | 260/673.5 |
| 3,849,507 | 11/1974 | Zuich | 260/671 C |
| 4,153,638 | 5/1979 | Bercik et al. | 585/526 |
| 4,299,730 | 11/1981 | Sommer et al. | 252/435 |
| 4,351,980 | 9/1982 | Reusser et al. | 585/820 |
| 4,367,352 | 1/1983 | Watts, Jr. et al. | 585/526 |
| 4,380,509 | 4/1983 | Sommer et al. | 502/439 |
| 4,456,779 | 6/1984 | Owen et al. | 585/415 |
| 4,480,142 | 10/1984 | Cobb | 585/464 |
| 4,531,014 | 7/1985 | Gregory et al. | 585/415 |
| 4,604,491 | 8/1986 | Dressler et al. | 585/26 |
| 4,808,559 | 2/1989 | Sommer et al. | 502/63 |
| 4,827,064 | 5/1989 | Wu | 585/530 |
| 4,879,425 | 11/1989 | Kukes et al. | 585/350 |
| 5,053,569 | 10/1991 | Marquis et al. | 585/255 |

OTHER PUBLICATIONS

Kuliev et al., "Preparation of High-Viscosity Synthetic Lubricants Using an Aluminosilicate Catalyst," Institute of Petrochemical Processes of the Academy of Sciences of the Azerbaidzhan an SSR, *Azerbaidzhanskoe, Neftiano, Khoziaistvo*, 1983, No. 4, pp. 40-43.

Figueras, "Pillared Clays as Catalysts," *Catal. Rev.-Sci. Eng.*, 30, pp. 457-499 (1988).

Friedlander, "Organized Polymerization. I. Olefins on a Clay Surface," *Journal of Polymer Science: Part C*, No. 4, pp. 1291-1301.

Friedlander et al., "Organized Polymerization III. Monomers Intercalated in Montmorillonite," *Polymer Letters*, vol. 2, pp. 475-479 (1964).

"Intercalated Catalysts and Pillared Clays," from a Process Evaluation/Research Planning Report, Chem Systems, titled Catalysts: Selected Developments, 84-3, pp. 239-249 (Dec. 1985).

Bolan, "Synthetic Lubricant Base Stocks," Process Economics Program Report No. 125A, SRI International, Apr. 1989 and Supplemental A, Sep. 1989.

"Synthetic Lubricants from Internal Olefins," Process Evaluation/Research Planning Report, Chem Systems, 84-Q-1, pp. 17-45.

Adams, "Synthetic Organic Chemistry Using Pillared, Cation-Exchanged and Acid-Treated Montmorillonite Catalysts—A Review", *Applied Clay Science*, 2 (1987) pp. 309-342.

Adams et al., "Clays as Selective Catalysts in Organic Synthesis," *Journal of Inclusion Phenomena*, vol. 5, (1987), pp. 663-674.

Laszlo and Cornelis, "CLAYCOP, A User Friendly Oxidizing and Nitrating Reagent," *Alrichimica Acta*, vol. 21, No. 4 (1988).

Chaudhuri and Sharma, "Some Novel Aspects of the Dimerization of α-Methylstyrene with Acidic Ion-Exchange Resins, Clays, and Other Acidic Materials as Catalysts," *Ind. Eng. Res.*, vol. 28, pp. 1757-1763 (1989).

Purnell, "Catalysis by Ion-Exchanged Montmorillonites", *Catalysis Letters*, 5 (1990), pp. 203-210.

Primary Examiner—Patrick P. Garvin
Assistant Examiner—E. D. Irzinski
Attorney, Agent, or Firm—Jack H. Park; Kenneth R. Priem; Russell R. Stolle

[57] ABSTRACT

An improved process is disclosed for preparing synthetic lubricant base stocks. Synthetic lubricant base stocks are prepared in good yield by oligomerizing linear olefins using certain acidic calcium montmorillonite clay catalysts which have aluminum nitrate deposited thereon.

23 Claims, No Drawings

PROCESS FOR OLIGOMERIZING OLEFINS USING AN ALUMINUM NITRATE-TREATED ACIDIC CLAY

CROSS-REFERENCE TO RELATED APPLICATION

This application is related to co-pending U.S. patent application Ser. No. 07/500,631, filed Mar. 28, 1990, which relates to the preparation of synthetic lubricant base stocks by oligomerizing linear olefins by means of certain acidic montmorillonite clays, and to co-pending U.S. patent application Ser. No. 07/516,931, filed Apr. 30, 1990, which relates to the preparation of synthetic lubricant base stocks having improved properties, made by oligomerizing mixtures of internal and alpha-olefins by means of certain acidic montmorillonite clay catalysts.

BACKGROUND OF THE INVENTION

1. Field of the Invention

The invention relates to the preparation of synthetic lubricant base stocks, and more particularly to synthetic lubricant base stocks made by oligomerizing linear olefins by means of certain aluminum nitrate-treated acidic montmorillonite clays.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of the base stocks is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_3$ raises environmental concerns. Thus, a method for oligomerizing long-chain olefins using a non-hazardous, non-polluting catalyst would be a substantial improvement in the art.

Kuliev et al. attempted to prepare synthetic lubricants by oligomerizing long-chain ($C_9$-$C_{14}$) olefins using non-hazardous and non-polluting acidic clays comprising sulfuric and hydrochloric acid-activated bentonites from the Azerbaidzhan SSR. See Kuliev, Abasova, Gasanova, Kotlyarevskaya, and Valiev, "Preparation of High-Viscosity Synthetic Lubricants Using an Aluminosilicate Catalyst," Institute of Petrochemical Processes of the Academy of Sciences of the Azerbaidzhan SSR, Azer. Neft. Khoz., 1983, No. 4, pages 40-43. However, Kuliev et al. concluded that "it was not possible to prepare viscous or high-viscosity oils by olefin polymerization over an aluminosilicate catalyst" and that "hydrogen redistribution reactions predominate with formation of aromatic hydrocarbon, coke, and paraffinic hydrocarbon." Gregory et al., on the other hand, used Wyoming bentonite to oligomerize shorter-chain olefins. (See U.S. Pat. No. 4,531,014.) However, like Kuliev et al., they also were unable to obtain a product high in dimer, trimer and tetramer, and low in disproportionation products.

Applicants discovered that it is possible to prepare synthetic lubricant base stocks in good yield by oligomerizing long-chain olefins using certain acidic montmorillonite clay catalysts. Applicants found that a high conversion of long-chain olefin to dimer, trimer, and tetramer may be obtained with formation of very little concomitant hydrogen redistribution by-product by using an acidic calcium montmorillonite clay having a moisture content ranging up to about 20 wt.%, a residual acidity in the range of about 3 to about 30 mg KOH/g (when titrated to a phenolphthalein end point), and a surface area of about 300 M$^3$/g or greater. In addition to being excellent catalysts, these clays are non-hazardous and non-polluting. With respect to the present invention, Applicants have discovered, surprisingly, that an even higher conversion of olefin to oligomer may be obtained where these acidic calcium montmorillonite clays are treated with aluminum nitrate prior to their use as a catalyst. Additionally, the resulting oligomer products contain a greater percentage of trimer and higher oligomers.

SUMMARY OF THE INVENTION

The invention relates to a process for the preparation of oligomers, comprising contacting a linear olefin having at least 10 carbon atoms with a catalyst comprising an aluminum nitrate-treated acidic calcium montmorillonite clay having a moisture content ranging up to about 20 wt.%, a residual acidity in the range of about 3 to about 30 mg KOH/g (when titrated to a phenolphthalein end point), and a surface area of about 300 M$^2$/g or greater.

DESCRIPTION OF THE PREFERRED EMBODIMENTS

Applicants discovered that synthetic lubricant base stocks may be prepared in good yield by oligomerizing long-chain olefins using certain acidic montmorillonite clay catalysts. Applicants have further discovered that an improvement in the conversion of olefin to oligomer and in the resulting dimer/trimer ratio may be obtained where these clays are treated with aluminum nitrate prior to their use as a catalyst.

The olefin monomer feed stocks used in the present invention may be selected from compounds comprising (1) alpha-olefins having the formula R"CH=CH$_2$, where R" is an alkyl radical of 8 to 22 carbon atoms, and (2) internal olefins having the formula RCH=CHR', where R and R' are the same or different alkyl radicals of 1 to 20 carbon atoms, provided that the total number of carbon atoms in any one olefin shall be within the range of 10 to 24, inclusive. A preferred range for the total number of carbon atoms in any one olefin molecule is 12 to 18, inclusive, with an especially preferred range being 13 to 16, inclusive. Mixtures of internal and alpha-olefins may be used, as well as mixtures of olefins having different numbers of carbon atoms, provided that the total number of carbon atoms in any one olefin shall be within the range of 10 to 24, inclusive. The alpha and internal-olefins to be oligomerized in this invention may be obtained by processes wellknown to those skilled in the art and are commercially available.

The oligomerization reaction may be represented by the following general equation:

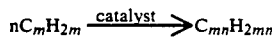

where n represents moles of monomer and m represents the number of carbon atoms in the monomer. Thus, the oligomerization of 1-decene may be represented as follows:

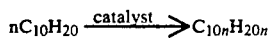

The reaction occurs sequentially. Initially, olefin monomer reacts with olefin monomer to form dimers. The dimers that are formed then react with additional olefin monomer to form trimers, and so on. This results in an oligomer product distribution that varies with reaction time. As the reaction time increases, the olefin monomer conversion increases, and the selectivities for the heavier oligomers increase. Generally, each resulting oligomer contains one double bond.

The clays to be aluminum nitrate-treated according to the present invention are certain silica-alumina clays, also called aluminosilicates. Silica-alumina clays primarily are composed of silicon, aluminum, and oxygen, with minor amounts of magnesium and iron in some cases. Variations in the ratios of these constituents, and in their crystal lattice configurations, result in some fifty separate clays, each with its own characteristic properties.

One class of silica-alumina clays comprises smectite clays. Smectite clays have a small particle size and unusual intercalation properties which afford them a high surface area. Smectites comprise layered sheets of octahedral sites between sheets of tetrahedral sites, where the distance between the layers can be adjusted by swelling, using an appropriate solvent. Three-layered sheet-type smectites include montmorillonites. The montmorillonite structure may be represented by the following formula:

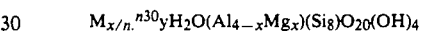

where M represents the interlamellar (balancing) cations, normally sodium or lithium; and x, y and n are integers.

Montmorillonite clays may be acid-activated by such mineral acids as sulfuric acid and hydrochloric acid. Mineral acids activate montmorillonites by attacking and solubilizing structural cations in the octahedral layers. This opens up the clay structure and increases surface area. These acid-treated clays act as strong Bronsted acids. Applicants have discovered that certain acid-treated montmorillonite clay catalysts are particularly effective for preparing synthetic lubricant base stocks in good yield by oligomerizing long-chain olefins. These clays are acidic calcium montmorillonite clays having a moisture content ranging up to about 20 wt.%, a residual acidity in the range of about 3 to about 30 mg KOH/g (when titrated to a phenolphthalein end point), and a surface area of about 300 M$^2$/g or greater. Illustrative examples include Filtrol grade 24, having a moisture content of 12 wt.%, a residual acidity of 8.5 mg KOH/g, and a surface area of 425 M$^2$/g; Filtrol grade 124, having a moisture content of 2 wt.%, a residual acidity of 7.0 mg KOH/g, and a surface area of 400 M$^2$/g; Filtrol grade 13, having a moisture content of 16 wt.%, a residual acidity of 15 mg KOH/g, and a surface area of 300 M$^2$/g; Filtrol grade 113, having a moisture content of 4 wt.%, a residual acidity of 10 mg KOH/g, and a surface area of 300 M$^2$/g; and Filtrol grade 224, having virtually no moisture, and having a residual acidity of 3.0 mg KOH/g, and a surface area of 350 M$^2$/g.

In the present invention, the clay is treated with aluminum nitrate prior to running the reaction. The clay should be added to a solution of about 1 to about 20 wt.%, preferably about 10 wt.%, aluminum nitrate in water. The ratio of clay to aluminum nitrate solution should be sufficient to provide a washed and dried catalyst having a concentration of aluminum nitrate at least sufficient to give the Friedel-Crafts effect, preferably about, 0.01 to about 10 wt.% aluminum nitrate, but not so much that it inhibits the clay's acid sites. The clay should remain in the aluminum nitrate solution for a period of time and under agitation to the extent necessary to meet these requirements.

Applicants also have found that advantageous results may be obtained when certain other Lewis Acid moderators are employed in the present invention in the place of aluminum nitrate. For example, acidic montmorillonite clays treated with either nickel chloride or zinc chloride were found to yield a higher conversion of monomer to oligomer, and to produce an oligomer product having a better dimer/trimer ratio, than untreated acidic clays. However, neither the nickel chloride-treated clay nor the zinc chloride-treated clay was capable of achieving the conversion and dimer/trimer ratio obtained with the aluminum nitrate-treated clay, the preferred Lewis Acid treatment in the present invention. Other Lewis Acids may provide comparable results. However, clays treated with either of two Lewis Acids, zirconium chloride and aluminum chloride, were found to produce a lower conversion of monomer to oligomer and/or a poorer dimer/trimer ratio than untreated clays.

Preferably, the aluminum nitrated-treated clay catalyst is heat-treated before running the reaction. Applicant found, surprisingly, that heat treatment of the catalyst prior to running the oligomerization reaction causes the catalyst to be more active and produce a higher olefin conversion. Additionally, clays heat-treated in this manner are more stable, remaining active during the oligomerization reaction for a longer period of time. The clays may be heat-treated at temperatures in the range of about 50° to 400° C., with or without the use of a vacuum. A more preferred temperature range is 50° to 300° C. Optionally, an inert gas may be used during heat treatment as well. Preferably, the clay should be heat-treated under conditions and for a length of time which will reduce the water content of the clay to approximately 1 wt.% or less.

The oligomerization reaction may be carried out in either a stirred slurry reactor or in a fixed bed continuous flow reactor. The catalyst concentration should be sufficient to provide the desired catalytic effect. The temperatures at which the oligomerization may be performed are between about 50° and 300° C., with the preferred range being about 150° to 180° C. The reaction may be run at pressures of from 0 to 1000 psig.

Following the oligomerization reaction, the unsaturated oligomers may be hydrogenated to improve their thermal stability and to guard against oxidative degradation during their use as lubricants. The hydrogenation reaction for 1-decene oligomers may be represented as follows:

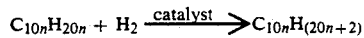

$$C_{10n}H_{20n} + H_2 \xrightarrow{catalyst} C_{10n}H_{(20n+2)}$$

where n represents moles of monomer used to form the oligomer. Hydrogenation processes known to those skilled in the art may be used to hydrogenate the oligomers. A number of metal catalysts are suitable for promoting the hydrogenation reaction, including nickel, platinum, palladium, copper, and Raney nickel. These metals may be supported on a variety of porous materials such as kieselguhr, alumina, or charcoal. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

While it is known to include a distillation step after the hydrogenation procedure to obtain products of various 100° C. viscosities, it is preferred in the method of the present invention that no further distillation (beyond monomer flashing) be conducted. In other words, the monomer-stripped, hydrogenated bottoms are the desired synthetic lubricant components. Thus, the method of this invention does not require the costly, customary distillation step, yet, surprisingly, produces a synthetic lubricant component that has excellent properties and that performs in a superior fashion. However, in some contexts, one skilled in the art may find subsequent distillation useful in the practice of this invention.

The monomer stripping step should be conducted under mild conditions. Distillation at temperatures exceeding 210° C. may cause the oligomers to break down in some fashion and come off as volatiles. Preferably, therefore, the reboiler or pot temperature should be kept at or under about 180° C. when stripping out the monomer.

The invention will be further illustrated by the following examples, which are given by way of illustration and not as limitations on the scope of this invention.

EXAMPLES

In the examples detailed below in Table I, the following procedures were used:

Aluminum Nitrate Treatment

To 100 cc of Harshaw/Filtrol Grade 24 granules was added 1 liter of 0.5 N aqueous aluminum nitrate solution. The mix was stirred mechanically for two days at room temperature. The solids were then filtered off and washed with distilled water until aluminum ions could no longer be detected in the washings. The remaining solids were then dried under a vacuum at 40° C. 108 g of while solid were recovered. Analysis showed the presence of 5.9 % aluminum.

Other Lewis Acid Treatments 100 cc samples of Harshaw/Filtrol Grade 24 granules were also treated, using the procedure detailed above, with aqueous solutions of the following Lewis Acids:

| Lewis Acid | Analysis of Treated Clay |
|---|---|
| AlCl$_3$ | Al, 6.5% |
| ZrCl$_4$ | Zr, 3.8% |
| NiCl$_2$ | Ni, 0.2% |
| ZnCl$_2$ | Zn, 1.3% |
| TiCl$_4$ | Ti, 5.1% |

Batch Oligomerizations

Olefin and clay catalyst were charged to a flask equipped with a stirrer, thermometer, heating mantle, and a water-cooled condenser (N$_2$ purge). The mixture was vigorously stirred and heated to a desired temperature for the desired time. The mixture was then cooled to ambient temperature and filtered with suction. The liquid was analyzed by liquid chromatography. The results are detailed in Table I.

TABLE 1

OLEFIN OLIGOMERIZATION USING ACIDIC CLAYS TREATED WITH ALUMINUM NITRATE AND OTHER LEWIS ACIDS

| EXAMPLE NO. | OLEFIN | (g) | CATALYST | (g) | TIME (HR.) | TEMP. (°C.) | CON. (%) | M (%) | D (%) | T+ (%) | D/T- RATIO |
|---|---|---|---|---|---|---|---|---|---|---|---|
| 1 | C-14A | 100 | H/F Clay-24 | 10.0 | 5.0 | 160 | 81.0 | 19.0 | 48.7 | 32.3 | 1.51 |
| 2 | C-14A | 100 | Al(NO$_3$)$_3$ on H/F-24 | 10.0 | 5.0 | 160 | 85.0 | 15.0 | 45.2 | 39.8 | 1.14 |
| 3 | C-14A | 100 | Al(NO$_3$)$_3$ on H/F-24 | 5.0 | 5.0 | 160 | 75.0 | 25.0 | 46.9 | 27.1 | 1.73 |
| 4 | C-14A | 100 | H/F Clay-24 | 10.0 | 6.0 | 150 | 76.8 | 23.2 | 47.0 | 29.1 | 1.62 |
| 5 | C-14A | 100 | Al(NO$_3$)$_3$ on H/F-24 | 10.0 | 6.0 | 150 | 80.2 | 19.8 | 47.5 | 32.8 | 1.45 |
| 6 | C-14A | 100 | Al(NO$_3$)$_3$ on H/F-24 | 10.0 | 4.0 | 180 | 82.3 | 17.7 | 50.8 | 31.5 | 1.61 |
| 7 | C-14A | 100 | H/F Clay-24 | 10.0 | 5.0 | 160 | 78.3 | 21.7 | 46.8 | 31.5 | 1.49 |
| 8 | C-1518-IO[1] | 100 | H/F Clay-24 | 10.0 | 5.0 | 180 | 67.4 | 32.6 | 47.3 | 19.1 | 2.48 |
| 9 | C-1510-IO | 100 | Al(NO$_3$)$_3$ on H/F-24 | 10.0 | 4.0 | 180 | 70.5 | 29.5 | 48.7 | 21.8 | 2.23 |
| 10 | C-14A | 100 | NiCl$_2$ on H/F-24 | 10.0 | 5.0 | 160 | 82.3 | 17.7 | 45.9 | 36.4 | 1.26 |
| 11 | C-14A | 100 | ZnCl$_2$ on H/F-24 | 10.0 | 5.0 | 160 | 83.2 | 16.8 | 43.1 | 37.6 | 1.15 |
| 12 | C-14A | 100 | ZrCl$_4$ on H/F-24 | 10.0 | 5.0 | 160 | 69.8 | 30.2 | 40.0 | 29.8 | 1.34 |
| 13 | C-14 | 100 | AlCl$_3$ on HF-24 | 10.0 | 5.0 | 160 | 80.3 | 19.7 | 48.4 | 31.9 | 1.52 |

Con. = Conversion; M = Monomer; D = Dimer; T+ = Trimer, plus Tetramer, Pentamer, etc.
A = Alpha
[1]Shell Chemical Co. Neodene ® 1518 Internal Olefin: 1.8% C$_{14}$ and lower; 25.3% C$_{15}$; 26.3% C$_{16}$; 24.2% C$_{17}$; 18.5% C$_{18}$; and 3.9% C$_{19}$.

We claim:

1. A process for the preparation of oligomers, comprising the following steps:
    (a) depositing a Lewis Acid, selected from the group consisting of aluminum nitrate, zinc chloride, and nickel chloride, on an acidic calcium montmorillonite clay having a moisture content ranging up to about 20 wt.%, a residual acidity in the range of about 3 to about 30 mg KOH/g and a surface area of about 300 M$^2$/g or greater, to provide a clay catalyst having a quantity of said Lewis Acid deposited thereon of at least about .01 wt.% ; and
    (b) contacting a linear olefin containing from 10 to 24 carbon atoms with a catalytically effective amount of the Lewis Acid-treated clay of step (a).

2. The process of claim 1, wherein the olefin contains from 12 to 18 carbon atoms.

3. The process of claim 1, wherein the moisture content of the clay prior to Lewis Acid treatment is about 12 wt.%, the residual acidity is about 8.5 mg KOH/g, and the surface area is about 425 M$^2$/g.

4. The process of claim 1, wherein the moisture content of the clay prior to Lewis Acid treatment is about 2 wt.%, the residual acidity is about 7.0 mg KOH/g, and the surface area is about 400 M$^2$/g.

5. The process of claim 1, wherein the moisture content of the clay prior to Lewis Acid treatment is about 16 wt.%, the residual acidity is about 15 mg KOH/g, and the surface area is about 300 M$^2$/g.

6. The process of claim 1, wherein the moisture content of the clay prior to Lewis Acid treatment is about 4 wt.%, the residual acidity is about 10 mg KOH/g, and the surface area is about 300 M$^2$/g.

7. The process of claim 1, wherein the moisture content of the clay prior to Lewis Acid treatment is essentially nil, the residual acidity is about 3.0 mg KOH/g, and the surface area is about 350 M$^2$/g.

8. A process for the preparation of oligomers, comprising the following steps:
    (a) depositing aluminum nitrate on an acidic calcium montmorillonite clay having a moisture content ranging up to about 20 wt.%, a residual acidity in the range of about 3 to about 30 mg KOH/g, and a surface area of about 300 M$^2$/g or greater, to provide a clay catalyst having a quantity of aluminum nitrate deposited thereon of from about 0.01 to about 10 wt.%; and
    (b) contacting a linear olefin containing from 10 to 24 carbon atoms with a catalytically effective amount of the aluminum nitrate-treated clay of step (a).

9. The process of claim 8, wherein the olefin contain from 12 to 18 carbon atoms.

10. The process of claim 8, wherein the moisture content of the clay prior to aluminum nitrate treatment is about 12 wt.%, the residual acidity is about 8.5 mg KOH/g, and the surface area is about 425 M$^2$/g.

11. The process of claim 8, wherein the moisture content of the clay prior to aluminum nitrate treatment is about 2 wt.%, the residual acidity is about 7.0 mg KOH/g, and the surface area is about 400 M$^2$/g.

12. The process of claim 8, wherein the moisture content of the clay prior to aluminum nitrate treatment is about 16 wt.%, the residual acidity is about 15 mg KOH/g, and the surface area is about 300 M$^2$/g.

13. The process of claim 8, wherein the moisture content of the clay prior to aluminum nitrate treatment is about 4 wt.%, the residual acidity is about 10 mg KOH/g, and the surface area is about 300 M$^2$/g.

14. The process of claim 8, wherein the moisture content of the clay prior to aluminum nitrate treatment is essentially nil, the residual acidity is about 3.0 mg KOH/g, and the surface area is about 350 M$^2$/g.

15. A process for the preparation of oligomers, comprising the following steps:
    (a) depositing aluminum nitrate on an acidic calcium montmorillonite clay having a moisture content ranging up to about 20 wt.%, a residual acidity in the range of about 3 to about 30 mg KOH/g, and a surface area of about 300 M$^2$/g or greater, to provide a clay catalyst having a quantity of aluminum nitrate deposited thereon of from about 0.01 to about 10 wt.%; and
    (b) heat-treating the aluminum nitrate-treated clay of step (a) to a moisture content of about 1 wt.% or less; and
    (c) contacting a linear olefin containing from 10 to 24 carbon atoms with a catalytically effective amount of the clay resulting from step (b).

16. The process of claim 15, wherein the olefin contains from 12 to 18 carbon atoms.

17. The process of claim 15, wherein the moisture content of the clay prior to aluminum nitrate treatment is about 12 wt.%, the residual acidity is about 8.5 mg KOH/g, and the surface area is about 425 M$^2$/g.

18. The process of claim 15, wherein the moisture content of the clay prior to aluminum nitrate treatment is about 2 wt.%, the residual acidity is about 7.0 mg KOH/g, and the surface area is about 400 M$^2$/g.

19. The process of claim 15, wherein the moisture content of the clay prior to aluminum nitrate treatment is about 16 wt.%, the residual acidity is about 15 mg KOH/g, and the surface area is about 300 M$^2$/g.

20. The process of claim 15, wherein the moisture content of the clay prior to aluminum nitrate treatment is about 4 wt.%, the residual acidity is about 10 mg KOH/g, and the surface area is about 300 M$^2$/g.

21. The process of claim 15, wherein the moisture content of the clay prior to aluminum nitrate treatment is essentially nil, the residual acidity is about 3.0 mg KOH/g, and the surface area is about 350 M$^2$/g.

22. A synthetic lubricant component, made by a process comprising the following steps:

(a) depositing aluminum nitrate on an acidic calcium montmorillonite clay having a moisture content ranging up to about 20 wt.%, a residual acidity in the range of about 3 to about 30 mg KOH/g, and a surface area of about 300 M$^2$/g or greater, to provide a clay catalyst having a quantity of aluminum nitrate deposited thereon of from about 0.01 to about 10 wt.%;

(b) contacting a linear olefin containing from 10 to 24 carbon atoms with a catalytically effective amount of the aluminum nitrate treated clay of step (a);

(c) separating out any remaining un-oligomerized olefin; and (d) hydrogenating the oligomer fraction resulting from
step, (c) to produce a synthetic lubricant component.

23. The synthetic lubricant component of claim 22, wherein the olefin contains from 12 to 18 carbon atoms.

* * * * *